US010667485B2

(12) United States Patent
Juarez et al.

(10) Patent No.: US 10,667,485 B2
(45) Date of Patent: *Jun. 2, 2020

(54) METHODS FOR WATERMELON PLANT AND SEED PRODUCTION

(71) Applicant: Seminis Vegetable Seeds, Inc., St. Louis, MO (US)

(72) Inventors: Benito Juarez, Woodland, CA (US); Terry Walker, Camarillo, CA (US); Fred McCuistion, Tifton, GA (US); Gregory E. Tolla, Woodland, CA (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 63 days.

This patent is subject to a terminal disclaimer.

(21) Appl. No.: 15/645,871

(22) Filed: Jul. 10, 2017

(65) Prior Publication Data
US 2017/0367278 A1 Dec. 28, 2017

Related U.S. Application Data

(60) Continuation of application No. 14/297,515, filed on Jun. 5, 2014, now abandoned, which is a division of application No. 12/549,259, filed on Aug. 27, 2009, now Pat. No. 8,772,582.

(60) Provisional application No. 61/093,131, filed on Aug. 29, 2008.

(51) Int. Cl.
A01H 6/34 (2018.01)
A01H 1/08 (2006.01)
A01H 5/08 (2018.01)
A01G 2/30 (2018.01)

(52) U.S. Cl.
CPC .............. A01H 6/342 (2018.05); A01G 2/30 (2018.02); A01H 1/08 (2013.01); A01H 5/08 (2013.01)

(58) Field of Classification Search
None
See application file for complete search history.

(56) References Cited

U.S. PATENT DOCUMENTS

| | | | |
|---|---|---|---|
| 4,936,904 | A | 6/1990 | Carlson |
| 5,007,198 | A | 4/1991 | Gray et al. |
| 6,018,101 | A | 8/2000 | Cheng et al. |
| 6,747,191 | B2 | 6/2004 | Zhang |
| 7,238,866 | B2 | 7/2007 | Zhang |
| 7,367,155 | B2 | 5/2008 | Kotyk et al. |
| 7,528,298 | B2 | 5/2009 | Zhang et al. |
| 2003/0217394 | A1 | 11/2003 | Zhang |
| 2005/0050597 | A1 | 3/2005 | Zhang et al. |
| 2009/0077683 | A1 | 3/2009 | Yang |
| 2009/0133141 | A1 | 5/2009 | Zhang et al. |

FOREIGN PATENT DOCUMENTS

| | | |
|---|---|---|
| JP | 2002-051655 | 2/2002 |
| KR | 10-2007-0091599 | 9/2007 |
| WO | WO 2000/070933 | 11/2000 |
| WO | WO 2006/014463 | 2/2006 |

OTHER PUBLICATIONS

Alan et al., "Effect of grafting on watermelon plant growth, yield and quality," J. of Agronomy, 6(2):362-365, 2007.
Boughalleb et al., "Resistance evaluation of grafted watermelon (Citrullus lanatus L.) against fusarium wilt and fusarium crown and root rot," Asian J. of Plant Pathology, 2(1):24-29, 2008.
Bruton et al., "The influence of rootstock selection on fruit quality attributes of watermelon," Open Food Sci. J., 3:15-34, 2009.
Cohen et al., "Introducing grafted cucurbits to modern agriculture: the Israeli experience," Plant Disease, 91(8):916-923, 2007.
Colla et al., "Effect of Salinity on Yield, Fruit Quality, Leaf Gas Exchange, and Mineral Composition of Grafted Watermelon Plants," HortSci 41(3): 622-627; 2006.
Cushman, "Grafting techniques for watermelon," Horticultural Sciences Department, Floriday Cooperative Extension Service, Institute of Food and Agricultural Sciences, University of Florida, Oct. 3, 2006.
Davis et al., "Cucurbit Grafting," Critical Reviews in Plant Science, 27(1):50-74, 2008.
Eigsti, "About our cover," HortScience, 6:2, 1971.
Furusato, Report of the Kihara Institute of Biological Sciences (Seiken Ziho) 5:125-128; 1952.
Jaskani et al., "Comparative study on vegetative, reproductive and qualitative traits of seven diploid and tetraploid watermelon lines," Euphytica, 145(3):259-268, 2005.
Kihara, "Tripolid watermelons," Proc. Amer. Soc. Hort. Sci., 58:217-230, 1951.
Kurata, "Cultivation of grafted vegetables II. Development of grafting robots in Japan," HortSci., 29(4):240-244, 1994.
Lee et al., "Advances in vegetable grafting," Horticultural Science Forum, Chronica Horticulturae, 43:13-19, 2003.
Lee, "Cultivation of grafted vegetables I. Current status, grafting methods, and benefits," HortSci., 29(4):235-239, 1994.
Levi et al., "Genetic diversity among lagenaria siceraria accessions containing resistance to root-knot nematodes, whiteflies, ZYMV or powdery mildew," Plant Genetic Resources, 7(3):216-226, 2009.
Love et al., "Controlled pollination transfer of nuclear male-sterile gene from a diploid to a tetraploid watermelon line," Euphytica, 35:633-638, 1986.
Miguel et al., "The grafting of triploid watermelon is an advantageous alternative to soil fumigation by methyl bromide for control of fusarium wilt," Scientia Horticulurae, 103(1):9-17, 2004.

(Continued)

Primary Examiner — David T Fox
(74) Attorney, Agent, or Firm — Dentons US LLP; Alissa Eagle, Esq.

(57) ABSTRACT

The invention provides methods for producing seeds in watermelon. In one embodiment methods are provided comprising grafting of a seed parent onto a stress tolerant rootstock, pollinating the seed parent with pollen from a pollen donor, and cultivating the seed parent until seed is formed. In specific embodiments, triploid seeds produced by a method of the invention are rendered conspicuously distinguishable from tetraploid seeds, and thus readily selected manually or by an automated machine. Methods for increasing seed yield and/or quality are also provided.

9 Claims, No Drawings

(56) References Cited

OTHER PUBLICATIONS

Miller et al. Washington State University Extensions, onlin http://vegetables.wsu.edu/WatermelonTable, pp. 1-3 (downloaded 2013).
Proietti et al., "Fruit quality of mini-watermelon as affected by grafting and irrigation regimes," *J. of Science of Food and Agriculture*, 88(6):1107-1114, 2008.
Rivero et al., "Role of grafting in horticultural plants under stress conditions," *Food, Agriculture & Environment*, 1(1):70-74, 2003.
Robinson, "In: Hybrid Seed Production: Rationale and Methods in Selected Crops," *Basra*, pp. 35, Food Products Press, Binghampton, NY, 2000.
Yang et al., "The effect of suboptimal temperature on germination of triploid watermelon seeds of different weights," *Seed Sci. and Technology*, 22(3):485-493, 1994. (Abstract).
Yetisir et al. "Rootstock Resistance to Fusarlum Wilt and effect on Watermelon Fruit Yield and Qualitym" *Phyotparasitica* 31(2): 163-169; 2003.
Zhang et al., "Cytological expression in the male-sterile ms mutant in watermelon," *J. of Heredity*, 85(4):279-285, 1994.
Zhang et al., "Development of genic male-sterile watermelon lines with delayed-green seedling marker," *HortScience*, 31(1):123-126, 1996.
Zhang et al., "Shoot regeneration from immature cotyledons of watermelon," Cucurbit Genetics Coop. Rep., 17:111-115, 1994.
Office Action issued in Korean Application No. 10-2011-7007050, dated Dec. 8, 2014.
Kremer-Kohne et al., "Approaches to solving the Hass small fruit problem: progress report," *South African Avocado Grower's Association Yearbook* 18:1-3, 1995.
Mesejo et al., "Gibberellic acid impairs fertilization in Clementine mandarin under cross-pollination conditions," *Plant Science* 175:267-271, 2008.
Kanda, "Watermelon: F1—hybrid seed production," *Vegetable Seed Production Technology of Japan Elucidated with Respective Variety Development Histories, Particulars*. Edited by S. Shinohara: Tokyo, 1984, vol. I, p. 318-339.
Shimotsuma, "Cytogenetical studies in the genus Citrullus, II: Intra- and interspecific hybrids obtained from all possible cross-combinations between diploid and tetraploid C. colocvnthis SCHRAD. and C. vulgaris SCHRAD," Seiken Ziho, 1959, vol. 10, p. 37-48.
Wall, "Use of marker genes in producing triploid watermelons," *Proceedings of the American Society for Horticultural Science* 76:577-581, 1960.
Shimotsuma, "Studies on triploid seed production in watermelons," *Japanese Journal of Breeding* 12:124-130, 1962.
Robinson, "Rationale and methods for producing hybrid cucurbit seed," *Journal of New Seeds* 1:1-47, 2000.
Jaskani et al., "Induction and Characterization of Tetraploid Watermelon," *J. Kor. Soc. Hort. Sci.* 45(2):60-65, 2004.
Rowe, "Breed Your Own Varieties," in Vegetable Seed Saving Handbook, obtained online from <http://howtosaveseeds.com/breeding.php>, accessed on Aug. 28, 2015.
Office Action issued in Mexican Patent Application No. MX/a/2011/002164, dated Jun. 19, 2015 (English translation).
Huh et al., *HortScience* 40(4):1053-1054 (Jul. 2005).
PI 482322 deposited in GRIN on Jan. 1, 1983.
Office Action regarding Mexican Patent Application No. MX/a/2011/002164, dated Aug. 30, 2016.
Free, "Las abejas son los diligentes polinizadores de las frutas y coltivos," available at http://www.fao.org/docrep/008/y5110s/5110s03.htm, dated 1999.
Luruena, "Lo que exconde la sandia sin semillas," available at http://www.gominolasdepetroleo.com/2013/09/lo-que-esconde-la-sandia-sin-semillas.html, dated Sep. 6, 2013.
Gómez et al "Seedless watermelon obtained without pollinating," Instituto Valenciano de Investigaciones Agrarias, Moncada (España), pp. 47-56, 2003.
Del Carmen Vidal et W., "Epecificity and pollination niche of plant species in a secondary deciduous forest," Ecotrópicos 18(2):73-88, 2005.

METHODS FOR WATERMELON PLANT AND SEED PRODUCTION

This application is a continuation of U.S. application Ser. No. 14/297,515, filed Jun. 5, 2014 (abandoned), which application is a divisional of U.S. application Ser. No. 12/549,259, filed Aug. 27, 2009, now U.S. Pat. No. 8,772,582, which application claims priority to U.S. Provisional Application Ser. No. 61/093,131, filed on Aug. 29, 2008, the disclosures of which are incorporated herein by reference in their entireties.

FIELD OF THE INVENTION

The present invention relates to the field of seed production and, more specifically, to methods of producing seeds of watermelon and other species.

BACKGROUND OF THE INVENTION

Watermelons are natural diploids, referred to as 2N (N=11). Many plants, including watermelons, can undergo a duplication of their entire set of chromosomes and exist as tetraploids 4N (4N=44). Watermelon tetraploids can be produced routinely in the laboratory using cell biology techniques.

A tetraploid parent can be crossed with a diploid parent to produce triploid seeds (3N=33). A hybrid triploid plant produces watermelon fruit which is "seedless," meaning that it very rarely produces mature seeds, and only rarely produces immature seeds with hard seed coats, but no embryo. To obtain triploid watermelon seed, a cross between a tetraploid and diploid line is made. The tetraploid female flower is used as the 'seed parent' and the diploid male flower is used as the pollen donor. Seeds obtained from this cross bear triploid embryos. A tetraploid seed parent typically produces only 5 to 10% as many seeds as a typical diploid plant. If female diploid flowers are pollinated with pollen coming from tetraploid flowers the result is empty seeds.

When production of triploid hybrids is done by open pollination, there is no control on the source of pollen that reaches the stigma of the tetraploid flower, and thus both tetraploid and triploid seeds may be found in the same fruit. In the absence of selection methods, hybrid seeds produced in this manner may therefore be contaminated with seeds resulting from self-pollination.

SUMMARY OF THE INVENTION

In one aspect, the invention provides a method of producing hybrid watermelon seed comprising: (a) obtaining a first watermelon plant, wherein the plant has been grafted onto a rootstock that exhibits resistance to at least one biotic and/or abiotic stress when under stress conditions; (b) allowing the grafted first watermelon plant to be pollinated by a second watermelon plant to produce a hybrid watermelon seed; and (c) allowing hybrid watermelon seed to form. In one embodiment, the first watermelon plant is a tetraploid watermelon plant that produces triploid (3N) hybrid seeds after being pollinated by a second watermelon plant that is diploid. In another embodiment, the first watermelon plant is a diploid watermelon plant that produces a diploid (2N) hybrid seed after being pollinated by a second diploid watermelon plant. In some embodiments, the second diploid watermelon is grafted onto a rootstock that exhibits a selected desirable phenotype.

A rootstock used in accordance with the invention may exhibit any type of stress resistance. In one embodiment, the rootstock exhibits tolerance to an abiotic stress selected from the group consisting of cold tolerance, heat tolerance, drought tolerance, and salt tolerance. In another embodiment, the rootstock exhibits biotic stress tolerance selected from the group consisting of disease resistance, insect resistance, and nematode resistance. Disease resistance includes resistance to bacterial, fungal, and viral diseases. In specific embodiments, the rootstock may be obtained from a plant selected from the group consisting of watermelon, squash, pumpkin, wax gourd, and bottle gourd. In further embodiments, the seed parent may or may not be grown under stress conditions.

Grafting carried out in accordance with the invention may be performed by any method known to one of skill in art. In one embodiment, grafting is performed by a method selected from the group consisting of splice grafting, bud grafting, cleft grafting, side grafting, approach grafting, and hole insertion grafting. Pollination may be carried out in accordance with standard methods, including pollination by insects and hand-pollination.

In another aspect of the invention, methods are provided for producing triploid seed, wherein the triploid seeds are rendered conspicuously distinguishable from the seeds of the tetraploid parent, such as based on size and/or shape, particularly when seed parent is exposed to stress conditions during cultivation. Thereby, the invention allows selecting the seeds of one ploidy category from the seeds of other ploidy categories based on size and/or shape. In one embodiment, the selection may be performed manually. In another embodiment, the selection may be performed mechanically by an automated machine.

The invention further permits producing increased number of fruits, increased number of seeds per fruit, and increased total seed weight per fruit in a grafted seed parent relative to a non-grafted seed parent. In specific embodiments, the seed yield per fruit, including diploid and tetraploid plants, may be defined as, for example, at least about 5, 10, 25, 50, at least about 75, at least about 100, at least about 125, at least about 150, at least about 175, at least about 200, at least about 225 or at least about 250 seeds per fruit, including from about 5 to about 150, from about 34 to about 100, from about 60 to about 120, from about 50 to about 150, from about 100 to about 200, from about 125 to about 250, and from about 150 to about 200, seeds per fruit produced by using a grafted seed parent with a diploid pollen donor plant. In the case of diploid watermelon plants, the seed yield per fruit may be defined in specific embodiments as at least about 150, 200, 250, 300, 350 or at least about 400.

In yet another aspect, the invention provides seeds and plants produced by a process that comprises crossing a first parent plant with a second parent plant, wherein at least one of the first or second parent plants is a plant grafted on a rootstock. In one embodiment of the invention, seed and plants produced by the process are first generation ($F_1$) hybrid seeds and plants produced by crossing a plant in accordance with the invention with another, distinct plant. Therefore, certain exemplary embodiments of the invention provide an $F_1$ hybrid seed and plant thereof. In specific embodiments of the invention, a diploid watermelon variety is used as the seed parent and the pollen donor is a second diploid watermelon plant. In other embodiments, the seed and pollen parents are a plant species selected from the group consisting of hot pepper, sweet pepper, tomato, squash, cucumber, pumpkin, gourd, melon, eggplant, and okra.

In still yet another aspect, the invention provides a population of seed parent and pollen donor parent plants in accordance with the invention. In one embodiment, a population of plants is provided planted in pollinating proximity in a field comprising a) tetraploid watermelon seed parent plants, wherein the plants have been grafted onto a rootstock that exhibits stress tolerance when under stress conditions; and b) diploid watermelon pollen donor plants. In specific embodiments, the tetraploid watermelon seed parent plants and diploid watermelon pollen donor plants are planted in alternating rows, and may be planted in a ratio of rows of tetraploid watermelon seed parent plants to diploid watermelon pollen donor plants of, for example, 1:1, 2:1, 3:1, 4:1 or 5:1.

These and other features and advantages of this invention are described in, or are apparent from, the following detailed description of various exemplary embodiments of the devices and methods according to this invention.

DETAILED DESCRIPTION OF THE INVENTION

The invention overcomes limitations in the art by providing improved methods for producing watermelon seeds. In one embodiment of the invention, the inventors surprisingly found that production of triploid seeds can be substantially improved by crossing a diploid pollen donor line with a tetraploid seed parent that has been grafted to a rootstock exhibiting resistance to biotic or abiotic stress when under stress conditions, and that these benefits are observed even in the absence of exposure of the seed parent to stress to which the rootstock confers resistance. For example, use of a disease resistant rootstock was found to confer improved seed production even in the absence of disease pressure. Significantly, the inventors also found that triploid seeds produced by the grafted seed parents exhibited a morphology that was more distinct from tetraploid seeds relative to ungrafted plants. The improved distinctions in seed morphological characteristics is of great importance due to the difficulty that can occur in distinguishing the tetraploid seeds also found in fruits of the seed parent from triploid seeds. By improving the distinctions between triploid and tetraploid seeds, such as in thickness and weight, the invention allows easy separation of the triploid seeds by manual or automated screening. Seed quality and the efficiency of seed production is thereby increased, benefiting seed producers and farmers alike.

In accordance with the invention, grafted seed parents may also be used to improve seed yield and quality. The inventors surprisingly found that increased numbers of seeds per fruit could be obtained in grafted seed parents relative to non-grafted seed parents, and even more surprisingly the effect was found even in the absence of stress to which the rootstock confers resistance. One embodiment of the invention therefore comprises crossing a grafted seed parent, which may be a diploid or tetraploid watermelon plant, with a grafted or ungrafted pollen donor plant. Examples of diploid seed lines that may be used as seed parents or pollen donors in accordance with the invention are well known in the art and include, but are not limited to, Allsweet, Crimson Sweet, Jubilee, Dixie Lee, Sugar Baby, Calsweet, Charleston Grey, and Minilee.

The techniques of the invention are also applicable to other species which are amenable to grafting. Therefore the invention provides, in one embodiment, a method of producing plant seed comprising: crossing a first plant that has been grafted onto a rootstock that exhibits stress tolerance when under stress conditions, allowing the first plant to be pollinated by a second plant of the same species, and allowing seed to form on the first plant, wherein the first plant is grown in the absence of said stress conditions. Examples of species applicable to the method include hot pepper, sweet pepper, tomato, squash, cucumber, pumpkin, gourd, melon, eggplant, and okra. In one embodiment, the rootstock confers resistance to bacterial, fungal and/or viral disease.

In another embodiment, a seed parent used in accordance with the invention is a tetraploid plant that is crossed to a diploid pollen donor to produce triploid hybrid seed. Examples of tetraploid seed parents that may be used are known in the art. Methods for producing tetraploid watermelon plants are also known in the art and are described in, for example, see Kihara, 1951 and Eigsti, 1971. To develop a tetraploid, chemicals that alter mitosis of a diploid inbred line may be used so that unusual numbers of chromosomes are obtained. For example, colchicine is a chemical that alters the mitotic spindle fibers of diploid cells resulting in a number of cells that are tetraploid. The diploid line used to create a tetraploid may be selected based on the traits desired for the tetraploid line. Traits that are desired for a tetraploid line may therefore first be introgressed into the diploid inbred lines that will be used to develop the tetraploid lines by breeding methods well known to one of skill in the art. Thus, the diploid and tetraploid parent lines may be bred separately for the desired traits.

Two generations of self-pollination and selection may be needed to "fix" the 4N condition because, after the colchicine treatment, chromosomal aberrations are often encountered that affect seed fertility, and must be eliminated. Once the stable tetraploid containing the desired characteristics is verified, it then can be used as a stable female parent for the production of the triploid hybrid.

Crossing two different tetraploids followed by recombination breeding can also result in new tetraploid lines. A longer breeding period is required to develop a stable tetraploid line using this approach. This is due to the larger number of genetic combinations and the fewer seed that tetraploids produce.

Seed parents may also be propagated by tissue culture. The use of tissue culture to propagate watermelon plants is exemplified in Zhang et al., 1994a.

Selection and Use Rootstock

In another aspect, the invention provides methods involving selecting and using a rootstock having a desired phenotype comprising tolerance to stress when under stress conditions. In one embodiment it may be desirable to select rootstock exhibiting desirable traits lacking in the seed parent. For instance, if a tetraploid seed parent is susceptible to a soil borne disease, a rootstock that is resistant to the soil borne disease may be selected for grafting.

Examples of abiotic stress that rootstock may confer resistance to include, but are not limited to, cold, high temperature, salt, drought, and flood. Examples of biotic stress include, but are not limited to, plant pathogens, insects, and nematodes. Rootstocks may be from plants of any ploidy level, including diploid and tetraploid plants. Examples of known rootstocks include, but are not limited to, RS-841, Shintoza, Shogun, Charmtoza, FR Couple, and FR Strong.

It is not necessary that the rootstock be from the same species from which the scion is derived. Rootstocks of other plants that are compatible with the scion may also be used. Examples of such compatible rootstocks for use with watermelon and other species include, but are not limited to, bottle gourd (*Lagenaria Siceraria* var. *hispida*), wax gourd (*Benincasa hispida*), pumpkin (*Cucurbita pepo*), squash (*Cucurbita moschata*), African horned cucumber (*Cucumis metuliferus*), *Cucurbita maxima*, interspecific *Cucurbita maxima*×*Cucurbita moschata* and bur-cucumber *Sicyos angulatus*. (See e.g., Zhang et al., 1994a).

Rootstock may also be a progeny of an interspecific cross. In a particular embodiment, the rootstock is a progeny of interspecific cross between *Cucurbita maxima* and *Cucurbita moschata*. An example of such progeny is Shintoza.

Grafting methods for watermelon and other species are known in the art. Examples of grafting methods include, but are not limited to, splice grafting, side grafting, approach grafting, hole insertion grafting, bud grafting, and cleft grafting. (See e.g., Cushman 2006). The grafting may be performed manually or by an automated machine.

Selecting Diploid Pollen Donors and Crossing with Seed Parents

In particular embodiments of the invention, diploid pollen donor plants are selected for use as a male parent in a cross with a grafted tetraploid or diploid plant. A stable diploid inbred may be selected. Adequate viable pollen supply from the diploid pollen donor may be needed for the female flowers to set and develop into regular fruit. In some embodiments, a diploid pollen donor is grafted onto a selected rootstock. In other embodiments, the diploid pollen donor is a non-grafted plant. In one non-limiting embodiment, the diploid pollen donor plant may be a publicly available line such as, for example, Crimson Sweet, Jubilee, Sugar Baby, Dixie Lee, Allsweet, Calsweet, Charleston Grey, and Minilee. Generally pollen donors will be selected that produce progeny with desirable phenotypes when crossed with the corresponding seed parent.

In accordance with the invention, processes are provided for crossing a seed parent with a pollen donor. These processes may, in specific embodiments, be further exemplified as processes for preparing hybrid watermelon seed or plants, wherein a seed parent is crossed with a pollen donor watermelon plant of a different, distinct line to provide a hybrid that has a grafted watermelon plant as one of its parents. In these processes, crossing will result in the production of seed. The seed production occurs regardless of whether the seed is collected.

In one embodiment of the invention, the first step in "crossing" comprises planting of seed parents and pollen donors in proximity so that pollination will occur, for example, mediated by insect vectors. In some embodiments, pollen may be transferred manually. The desired ratio of seed parents and pollen donors for watermelon hybrid seed production is well known to one of skill in the art. In one example, the seed parents and pollen donors are planted at a ratio of 2:1. Examples of other ratios of seed parents and pollen donors include, but are not limited to, 1:1, 3:1, 4:1, and 5:1. In a particular embodiment, seed production fields may be planted at the ratio of 2 rows of female line and 1 row of diploid male line.

A second step may comprise cultivating or growing the seeds of seed parent and pollen donor watermelon plants into plants that bear flowers. A third step may comprise preventing self-pollination of the plants, such as by emasculating the male portions of flowers, (i.e., treating or manipulating the flowers to produce an emasculated parent watermelon plant). Self-incompatibility systems may also be used in some hybrid crops for the same purpose. Self-incompatible plants still shed viable pollen and can pollinate plants of other varieties but are incapable of pollinating themselves or other plants of the same line. In some embodiments, all the male flower portions may be manually removed from the female plants. This process is known as de-budding or emasculation. In other embodiments, a male-sterile seed parent line may be used that may not require the de-budding process.

A fourth step for a hybrid cross may comprise cross-pollination between the seed parent and pollen donor watermelon plants. In one embodiment, the pollen of the diploid pollen donor parent is transferred to a female diploid or tetraploid seed parent flower by manual methods well known to one of in the art. In another embodiment, the pollen is transferred by insect vectors. In a particular embodiment, the crossing of seed parents may involve self-pollination, which may occur manually or without any human intervention.

Yet another step comprises harvesting seeds from the seed parent. All or a portion of the fruit set on the seed parent can be harvested, and seeds are isolated. (U.S. Pat. No. 6,018, 101). The harvested seed can be used for any desired purpose, including grown to produce watermelon plants and sold to farmers.

Recovery of Seeds

Seeds may be recovered from matured fruits using methods known to one of skill in the art. In some embodiments, an open pollinated tetraploid seed parent may produce tetraploid seeds in addition to triploid seeds. For example, in order to reduce the cost and labor involved in hand pollination, the transport of the pollen may be left to bees in the field of open pollinated seed parents. Under these conditions, since there is no control on the source of pollen that reaches the stigma of the tetraploid flower, tetraploid and triploid seeds may be found in the same fruit.

In one example, a grafted tetraploid seed parent of the invention produces triploid seeds that are conspicuously distinguishable from tetraploid seeds based on size and/or shape. In specific embodiments, the grafted seed parent yields seeds with improved distinctions in seed thickness and/or seed weight between triploid and tetraploid seeds relative to a non-grafted seed parent. The grafted seed parent, even if raised under a stress condition, yields triploid seeds that are distinguishable from tetraploid seed and can be selected, for example, as being thinner than tetraploid seeds, weighing less than tetraploid seeds, and/or otherwise exhibiting morphological distinctions.

The triploid seeds may therefore be separated from the tetraploid seeds based on differences in morphological characteristics. In one embodiment, the seeds are manually separated. In another embodiment, the seeds are mechanically separated using an automated machine. The automated machine may separate the seeds in accordance with their thickness and/or weight.

In a further embodiment, the invention provides a plant of a grafted and hybridized seed parent that exhibits an average seed number of at least 50 seeds per fruit. In specific embodiments, the seed number may be further defined as, for example, at least about 50, at least about 75, at least about 100, at least about 125 or at least about 150 seeds per fruit, including from about 50 to about 150, from about 34 to about 100, and from about 60 to about 120 seeds per fruit produced by using a grafted seed parent with a diploid pollen donor plant.

In another embodiment, the invention provides a plant of a grafted and hybridized seed parent that exhibits an average seed weight of at least 8 grams (gms) per fruit. In specific embodiments, the seed weight may be further defined as, for example, at least about 0.5 gms, at least about 2 gms, at least about 5 gms, at least about 8 gms, at least about 10 gms, at least about 20 gms or at least about 50 gms per fruit, including from about 5 to about 50, from about 8 to about 40, and from about 8 to about 15 gms per fruit produced by using a grafted seed parent with a diploid pollen donor plant.

Male Sterility

In certain aspects, a seed parent plant may be a male sterile (i.e., comprise a male sterile scion). For example, a grafted tetraploid watermelon scion as described herein maybe male sterile. In certain aspects, a seed parent may be rendered male sterile by physical removal of male plant tissues such as removal of pollen producing flowers. In some aspects, a seed parent may be rendered male sterile by application of a gametocide, for example as described in U.S. Pat. No. 4,936,904. In still further aspects, a seed parent may comprises a male sterility trait such as genetic or cytoplasmic male sterility. For example, tetraploid watermelon plants comprising a recessive gene for male sterility were described by Love et al., 1986. A stable male recessive watermelon line, G17AB, has also been described (Zheng et al., 1994b; Zheng et al., 1996). Watermelon plants comprising a male sterility gene, such as the G17AB line, or progeny of such a plant or line of plants may also be used according to the methods described herein.

EXAMPLES

Example 1

Effect of Grafting of Seed Parent on Seed Numbers and Hybridity

Scions were obtained from the tetraploid watermelon hybrid variety TML 110-1440 and grafted onto the rootstocks Charmtoza, Shintoza, and Shogun. Grafting was carried out by side grafting. The grafted tetraploid was planted in a field together with non-grafted tetraploid plants and the diploid variety 110-6433 to serve as a male parent plant. The plants were grown under conditions in which the plants were not subject to disease pressure or other stress of note.

Insect-mediated pollination was allowed to occur between the diploid and grafted tetraploid plants and seeds were allowed to form. Seeds were then harvested from the tetraploid parent and measurements taken of seed weight, seed number, and hybridity (% hybridity represent the % of triploid seed in the fruit of the tetraploid parent). The results are presented in Table 1

TABLE 1

Increased seed weight per fruit, seed number per fruit and hybridity resulted from grafting of seed Parents.

| | Total Number of Fruits | Total Seed Weight (Gms.) | Clean/sized Wt. (Gms.) | Total Number of seeds | Grams per fruit | Number of seeds per fruit | Hybridity (%) |
|---|---|---|---|---|---|---|---|
| Non Grafted | 35 | 348.53 | 347.80 | 5,015 | 9.96 | 143 | 65.40 |
| Grafted (all) | 60 | 689.90 | 691.20 | 9,753 | 11.50 | 163 | 81.83 |
| Grafted Charmtoza | 15 | 166.30 | 166.50 | 2,488 | 11.09 | 166 | 78.70 |
| Grafted Shintoza | 32 | 372.34 | 373.10 | 5,359 | 11.64 | 167 | 87.20 |
| Grafted Shogun | 13 | 151.26 | 151.60 | 1,906 | 11.64 | 147 | 79.60 |

As shown, in Table 1, the grafted plants yielded the total seed weight per fruit of 11.50 gms, but the non-grafted plants yielded the total seed weight per fruit of only 9.96 gms. Also, the grafted plants yielded an average of 163 seeds per fruit, but the non-grafted plants yielded an average of only 143 seeds. The grafted plants yielded the hybridity of 81.83%, but the non-grafted plants yielded the hybridity of only 65.40%.

Example 2

Effect of Grafting of Seed Parent on Fruit Yield, Seed Weight and Hybridity

The tetraploid seed parent TML 110-1440 was grafted on the rootstocks, Shintoza, Shogun, Charmtoza, FR Couple, and FR Strong by side grafting. The grafted tetraploid plants, non-grafted tetraploid and the diploid pollen donor line 110-6433 were planted in a field and cultivated to maturity. Diploid pollen donors were planted along with the grafted tetraploid seed parents, with spacings of 16"×16", 32"×32", 48"×48", and 24"×24".

The tetraploid seed parents were open-pollinated by insects and seeds were allowed to form. Seeds were harvested and the seed weight, seed number, and hybridity measured. The results are provided in Table 2.

TABLE 2

Increased seed weight per fruit, and hybridity resulted from grafting of seed parents.

| | Spacing (inches) | Gr./plant | # of fruit/plant | TSW (Thousand Seed Weight) gms | Hybridity | Extended Yield Kg/Ac |
|---|---|---|---|---|---|---|
| Female parent, TML 110-1440 plus Rootstock | | | | | | |
| TML 110-1440 w/o rootstock | 16 | 9.2 | 1.15 | 70 | 87.2 | 60 |
| | 32 | 15.1 | 1.69 | 71 | 85 | 49 |
| | 48 | 18.5 | 1.57 | 70 | 89 | 40 |
| | 24 | 13 | 1.35 | 70 | 83.7 | 56 |
| | Manually self-pollinated | 4.2 | | 85 | | |
| | Manually cross-pollinated. | 7.6 | | 72 | | |
| Female parent, TML 110-1440 plus Rootstock | | | | | | |
| Shintoza | 16 | 14.5 | 1.45 | | 83 | 94 |
| | 32 | 30 | 2.5 | 67.95 | 88 | 98 |
| | 48 | 43 | 3.83 | 67.7 | 88 | 93 |
| | 24 | 15.9 | 2.32 | | 95.7 | 69 |
| | Manually self-pollinated | N/A | | | | |
| | Manually cross-pollinated | 6.4, 8.2 | | | | |
| Shogun | 16 | 12.8 | 1.4 | 74 | 84 | 83 |
| | 32 | 20.6 | 2.3 | 72 | 86 | 67 |
| | 48 | N/A | N/A | | | |
| | 24 | N/A | N/A | | | |
| | Manually self-pollinated | 4.3, 7.8 | | 76 & 80 | | |
| | Manually cross-pollinated | 20.9 | | 72 | | |
| Charmtoza | 16 | 16 | 1.7 | 72.05 | 83 | 104 |
| | 32 | 28.9 | 2.4 | 68 | 89 | 94 |
| | 48 | 29.3 | 3.2 | 72.1 | 87 | 63 |
| | 24 | 19.6 | 2.25 | 65.55 | 83.5 | 85 |
| | Manually self-pollinated | N/A | | | | |
| | Manually cross-pollinated | 8.4, 8.0 | | | | |
| FR Couple (TW 1) | 16 | 17.6 | 1.75 | | 70.7 | 114 |
| | 32 | 23.2 | 2.53 | 73.5 | 85 | 75 |
| | 48 | 32.6 | 3.3 | 73.2 | 82 | 71 |
| | 24 | 20.6 | 2.1 | 68.7 | 88.9 | 89 |
| | Manually self-pollinated | 3.5 | | | | |
| | Manually cross-pollinated | 10.7, 8.8 | | | | |
| FR Strong (TW 2) | 16 | 15.7 | 1.6 | 73.1 | 83.9 | 102 |
| | 32 | 25 | 2.3 | 74.15 | 80 | 81 |
| | 48 | 41.4 | 3.29 | 72.6 | 86 | 90 |
| | 24 | 21.5 | 2.38 | 67.75 | 83.3 | 93 |
| | Manually self-pollinated | N/A | | | | |
| | Manually cross-pollinated | 12.8, 9.1 | | | | |

As shown in Table 2, the seed parents grafted on the rootstocks Shintoza, Shogun, Charmtoza, FR Couple, and FR Strong yielded increased number of fruits, seed yield, total seed weight, and hybridity.

Example 3

The Effect of Grafting on Seed Numbers and Seed Yield

Tetraploid watermelon lines TML110-1440, TML110-0064, TCS110-1009, and TCS110-1018 were crossed as seed parent lines with a diploid pollen donor line. Prior to crossing tetraploid seed parents were grafted onto the inter-specific rootstock *Cucurbita maxima*×*Cucurbita moschata* (Shintoza) by side grafting. The diploid pollen donor plants were ungrafted.

Grafted and non-grafted tetraploid seed parent plants were transplanted on the same day into a field that was subject to normal (no stress noted) conditions during cultivation. The diploid pollen donor WAS110-6433 was planted with the tetraploid seed parent plants. The plants were grown to maturity with bee-mediated pollination of the tetraploid plants taking place. Fruits were harvested in different days considering the relative maturity to allow full development of seed parts. Seeds were extracted and the number of fruits, total seed weight, average seed weight per fruit, total seed numbers, and average seed number per fruit determined. The results are presented in Table 3.

TABLE 3

Increased seed weight and seed numbers per fruit resulting from grafting of seed parents

| Experimental Material | Number of Fruits | Total Seed Weight (Gms) | Avg. seed Wt. Per fruit (Gms) | Total Seed Count | Average Seed Number per fruit |
|---|---|---|---|---|---|
| B64 NG | 20 | 172.86 | 8.64 | 2,432 | 121 |
| B64 G | 19 | 182.59 | 9.61 | 2,825 | 148 |
| 1440 NG | 27 | 324.17 | 12 | 4,078 | 151 |
| 1440 G | 20 | 267.63 | 13.38 | 3,677 | 184 |
| 1009 NG | 19 | 176.82 | 9.3 | 2,297 | 121 |
| 1009 G | 15 | 121.02 | 8.07 | 1,854 | 124 |
| 1018 NG | 24 | 191.32 | 7.97 | 2,521 | 105 |
| 1018 G | 15 | 130.67 | 8.71 | 1,807 | 120 |

NG - Non-grafted;
G - Grafted

As shown in Table 3, grafted seed parents yielded greater weight and seed number per fruit relative to non-grafted seed parents. For example, the grafted B64 seed parent yielded 9.61 gms of seed per fruit, but the non-grafted B64 yielded only 8.64 gms of seed per fruit. Likewise, the grafted 1440 and 1018 plants yielded more seed weight per fruit relative to their non-grafted plants. The seed weight for grafted 1009 plants was lower than non-grafted plants, possibly because the trait controlling seed number per plant was segregating in this line and was unevenly represented between those plants selected for grafting relative to non-grafting. In addition, the grafted B64 seed parent yielded 148 seeds per fruit, while the non-grafted B64 yielded only 121 seeds per fruit, and each of the grafted 1440, 1009, 1018 plants yielded more seeds per fruit relative to their non-grafted plants.

Example 4

Seed Production in Melon and Watermelon Using Grafting

An analysis was also carried out on the effect on seed production (in grams per plant) using grafting with melon and watermelon varieties and varying rootstocks relative to nongrafted checks. The results of the analysis are presented below.

| | Trial Identification | Hectares planned | Planned plants | Hectares planted | Number plants that worked | Seed production in kilograms | Grams seed per plant | % germination |
|---|---|---|---|---|---|---|---|---|
| Melon Grafting Rootstock/Grafted Scion Chilsung Shintoza 145-22182 FPO 863991 | | | | | | | | |
| Graft | S6V1 | 0.34 | 5440 | 0.3 | 4790 | 92.72 | 19.3 | 94-97 |
| Non-graft check | S7V5,6 | | | 0.3 | 4790 | 77.82 | 16.25 | 94-98 |
| Melon Grafting Rootstock/Grafted Scion Gourd/145-23190 FPO 895010 | | | | | | | | |
| Graft | S5V1 | 0.46 | 7360 | 0.06 | 1000 | 3.68 | 3.68 | 87-96 |
| Non-graft check | L2V4 | | | 0.28 | 4602 | 42.07 | 9.14 | 95-100 |
| Melon Grafting Rootstock/Grafted Scion Chilsung Shintoza 145-23269 FPO 884417 | | | | | | | | |
| Graft | S6V1 | 0.59 | 9440 | 0.38 | 6043 | 7.24 | 1.2 | 42-84 |
| Non-graft check | S3V5,6 | | | 0.38 | 6043 | 73.61 | 12.18 | 71-94 |

-continued

|  | Trial Identification | Hectares planned | Planned plants | Hectares planted | Number plants that worked | Seed production in kilograms | Grams seed per plant | % germination |
|---|---|---|---|---|---|---|---|---|
| | Melon Grafting Rootstock/Grafted Scion Shintoza 145-23206 FPO 897683 | | | | | | | |
| Graft | L6V3 | 0.33 | 5280 | 0.1 | 1628 | 22.03 | 13.53 | 1628 |
| Non-graft check | S9V4,5 | | | 0.1 | 1628 | 18.66 | 11.46 | 1628 |
| | Melon Grafting Rootstock/Grafted Scion Shintoza 145-23304 FPO 880342 | | | | | | | |
| Graft | S5V1 | 0.16 | 2560 | 0.13 | 2136 | 31.1 | 14.56 | 73-93 |
| Non-graft check | L5V3,4 | | | 0.13 | 2136 | 36.5 | 17.08 | 96-99 |
| | Melon Grafting Rootstock/Grafted Scion Shintoza 145-23249 FPO 872648 | | | | | | | |
| Graft | S5V1 L6V3 | 0.33 | 5280 | 0.11 | 1829 | 18.26 | 9.98 | 84-86 |
| Non-graft check | L2V2 | | | 0.11 | 1829 | 28.85 | 15.77 | 84-98 |
| | Melon Grafting Rootstock/Grafted Scion Shintoza 145-22189 FPO 909292 Etapa 14 | | | | | | | |
| Graft | L 6V 4 | 0.59 | 9440 | 0.25 | 4053 | 67.95 | 16.76 | 90-93 |
| Non-graft check | LB,C V 18;18,19 | | | 0.25 | 1750 | 16.7 | 9.5 | 82-94 |
| | Melon Grafting Rootstock/Grafted Scion Shintoza 145-22189 FPO 909292 Etapa 15 | | | | | | | |
| Graft | DV19;S11V4,5 | 0.2 | 3200 | 0.11 | 1697 | 20.3 | 11.96 | 84-95 |
| Non-graft check | CV20,21,22 Gal | | | 0.11 | 1697 | 20.4 | 12.02 | 63-90 |
| Graft | L.6V4 | 0.19 | | | | | | |
| | Melon Grafting Rootstock/Grafted Scion Shintoza 145-23377 FPO 897686 | | | | | | | |
| Graft | L6V3,4 | 0.44 | 7040 | 0.18 | 2873 | 25.68 | 8.94 | 88-91 |
| Non-graft check | S 10V4,5 | | | 0.18 | 2873 | 18.09 | 6.3 | 48-95 |
| | Melon Grafting Rootstock/Grafted Scion Shintoza 145-23269 FPO 897686 | | | | | | | |
| Graft | S2V2,3; DV19 Gal | 0.14 | 2240 | 0.09 | 1411 | 15.7 | 11.12 | 88-94 |
| Non-graft check | CV27 Gal | | | 0.09 | 1411 | 22.53 | 15.96 | 68-94 |
| | Melon Grafting Rootstock/Grafted Scion Shintoza 145-311134 FPO 909289 | | | | | | | |
| Graft | DV19 Gal | 0.1 | 1600 | 0.08 | 1267 | 15.25 | 12 | 93-95 |
| Non-graft check | CV27 Gal | | | 0.08 | 1267 | 24.51 | 19.34 | 94-95 |

-continued

| | Trial Identification | Hectares planned | Planned plants | Hectares planted | Number plants that worked | Seed production in kilograms | Grams seed per plant | % germination |
|---|---|---|---|---|---|---|---|---|
| | Melon Grafting Rootstock/Grafted Scion Shintoza 145-297888 FPO 917028 | | | | | | | |
| Graft | S2V2,3; DV18 Gal | 0.36 | 5760 | 0.27 | 4103 | 49.29 | 12 | 96-95 |
| Non-graft check | Galmo DV18 | | | 0.27 | 4103 | 60.78 | 14.81 | 85-93 |
| | Melon Grafting Rootstock/Grafted Scion Rootstock/145-23269 FPO 925514 | | | | | | | |
| Charmtoza | S11V4,5 | 0.07 | 288 | 0.007 | 111 | 0.67 | 6 | |
| Chilsung Shimtoza | S11V4,5 | | 480 | 0.012 | 205 | 0.54 | 2.63 | |
| Shimtoza | S11V4,5 | | 460 | 0.01 | 169 | 0.09 | 0.53 | |
| Non-graft check | S11V4,5 | | | | 34023 | 494.32 | 14.53 | |
| | Melon Grafting Grafted Scion Rootstock/145-23269 FPO 925514 | | | | | | | |
| Hwangtoza | S10V2,3 | 0.59 | | 0.05 | 726 | 5.32 | 7.32 | |
| Shimtoza (0) | S10V2,3 | | | 0.02 | 311 | 1.77 | 5.69 | |
| Shimtoza (1) | S10V2,3 | | | 0.008 | 138 | 1.55 | 11.23 | |
| 145-22182 (IMPAC) | S10V2,3 | | | 0.11 | 1717 | 23.2 | 13.5 | |
| Non-graft check | S10V2,3 | | | | 34023 | 494.32 | 14.53 | |
| | Watermelon Grafting Rootstock/Grafted Scion Chilsung Shintoza/177-21153 FPO 880345 | | | | | | | |
| Graft | S4V1 | 0.58 | 9280 | 0.33 | 5284 | 201.83 | 38 | 98-99 |
| Non-graft check | L9V14 Gal | | | 0.33 | 5284 | 50.4 | 9.5 | 95-98 |
| | Watermelon Grafting Rootstock/Grafted Scion Chilsung Shintoza/177-25423 FPO 892024 | | | | | | | |
| Graft | S4,3V1;1 | 0.24 | 3840 | 0.15 | 2367 | 41.29 | 17.4 | 99-100 |
| Non-graft check | L12V4 Gal | | | 0.15 | 2367 | 19.26 | 8.1 | 99-100 |
| | Watermelon Grafting Rootstock/Grafted Scion Shintoza/177-152185 FPO 897682 | | | | | | | |
| Graft | S3V1 | 0.08 | 1280 | 0.05 | 863 | 3.45 | 3.99 | 96-99 |
| Non-graft check | L9V8,9 Gal | | | 0.05 | 863 | 6.12 | 7.09 | 97-99 |
| | Watermelon Grafting Rootstock/Grafted Scion Shintoza/177-268382 FPO 926134 | | | | | | | |
| Graft | L8V7 Gal | 0.1 | 1600 | 0.05 | 810 | 8.63 | 10.65 | 99-99 |
| Non-graft check | L8V7,8 Gal | | | 0.05 | 810 | 4.07 | 5.02 | 99-99 |
| | Watermelon Grafting Rootstock/Grafted Scion Shintoza 177-261691 FPO 909287 | | | | | | | |
| Graft | L8V9 Gal | 0.1 | 1600 | 0.06 | 981 | 8.53 | 8.69 | 98-99 |
| Non-graft check | L8V9,10 Gal | 0.5 | 8000 | 0.06 | 981 | 1.16 | 1.18 | 99-99 |

-continued

| | Trial Identification | Hectares planned | Planned plants | Hectares planted | Number plants that worked | Seed production in kilograms | Grams seed per plant | % germination |
|---|---|---|---|---|---|---|---|---|
| | Watermelon Grafting Rootstock/Grafted Scion Shintoza 178-295191 FPO 909287 | | | | | | | |
| Graft | L8V5 Gal. | 0.01 | 166 | 0.01 | 166 | 0.29 | 1.75 | |
| Non-graft check | L8V5,6 Gal. | | | 0.01 | 166 | 0.29 | 1.75 | |
| | Watermelon Grafting Rootstock/Grafted Scion Shintoza 178-213828 FPO 926141 | | | | | | | |
| Graft | L8V2,3 Gal. | 0.17 | 2720 | 0.06 | 998 | 0.41 | 0.41 | |
| Non-graft check | L8V4,5 Gal. | | | 0.06 | 998 | 0.38 | 0.38 | |

Example 5

Further Analysis of the Effect of Grafting on Seed Production

Grafted diploid watermelon varieties Starbrite and Susanita were grafted on rootstock varieties Charmtoza, Chilsung Shintoza, FR-Couple, and Hwangtoza. Seed yield per plant was measured in grams and indicated an increase in the seed yield per plant for most grafted combinations in comparison with the ungrafted check.

| VARIETY | ROOTSTOCK | FRUIT COUNT | YIELD | YIELD/ PLANT |
|---|---|---|---|---|
| STARBRITE | CHARMTOZA | 7 | 451 | 64.43 |
| | CHECK | 57 | 2145 | 37.63 |
| | CHILSUNG SHINTOZA | 28 | 1643 | 58.68 |
| | FR-COUPLE | 56 | 2118 | 37.82 |
| | HWANGTOZA | 47 | 2407 | 51.21 |
| SUSANITA | CHARMTOZA | 60 | 1314 | 21.90 |
| | CHECK | 69 | 1170 | 16.96 |
| | CHILSUNG SHINTOZA | 67 | 1584 | 23.64 |
| | FR-COUPLE | 64 | 1376 | 21.50 |
| | HWANGTOZA | 55 | 1409 | 25.62 |

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. Nos. 4,936,904; 6,018,101
Cushman, *Univ. of Florida, Extension Publication*, HS1075, 1-5, 2006.
Eigsti, *HortScience*, 6:1-2, 1971.
Kihara, *Proceedings of American Society for Horticultural Science*, 58:217-230, 1951.
Kurata, *HortScience* 29(4):235-239, 1994.
Love et al., *Euphytica*, 35:633-638, 1986.
Zhang et al., *Cucurbit Genetics Coop.*, 17:111-115, 1994a.
Zheng et al., *J. Heredity*, 85(4):279-285, 1994b.
Zheng et al., *HortScience*, 31(1):29-57, 123-126, 1996.

What is claimed is:

1. A tetraploid watermelon seed parent plant, wherein the seed parent plant has been grafted onto a rootstock that exhibits stress tolerance when under stress conditions, and wherein the seed parent plant has been pollinated by a diploid watermelon pollen donor plant.

2. A population of watermelon plants planted in pollination proximity in a field, said population comprising plants of the tetraploid watermelon seed parent plant of claim 1 and plants of a diploid watermelon pollen donor plant, wherein the tetraploid watermelon seed parent plants and diploid watermelon pollen donor plants are planted in different rows.

3. The seed parent plant of claim 1, wherein the seed parent plant has been hand pollinated with pollen from the diploid watermelon donor plant.

4. The seed parent plant of claim 1, wherein the seed parent plant has been pollinated by an insect with pollen from the diploid watermelon donor plant.

5. The seed parent plant of claim 1, wherein the rootstock exhibits disease resistance, insect resistance, nematode resistance or biotic stress tolerance.

6. The seed parent plant of claim 1, wherein the rootstock is from a watermelon, squash, pumpkin, wax gourd, or bottle gourd plant.

7. The seed parent plant of claim 1, wherein the seed parent plant has been cultivated in the absence of stress conditions.

8. The seed parent plant of claim 1, wherein the rootstock has been grafted onto the seed parent plant by splice grafting, bud grafting, cleft grafting, side grafting, approach grafting, or hole insertion grafting.

9. A population of watermelon seed parent plants according to claim 1.

* * * * *